United States Patent [19]

Spaulding et al.

[11] Patent Number: 4,845,103

[45] Date of Patent: Jul. 4, 1989

[54] NON-PARTICULATE, NON-FLOWABLE, NON-REPELLANT INSECTICIDE-BAIT COMPOSITION FOR THE CONTROL OF COCKROACHES

[75] Inventors: Laura Spaulding, Bloomfield; Nunzio R. Pasarela, Bridgewater, both of N.J.

[73] Assignee: American Cyanamid Company, Stamford, Conn.

[21] Appl. No.: 183,283

[22] Filed: Apr. 11, 1988

Related U.S. Application Data

[63] Continuation of Ser. No. 933,331, Nov. 19, 1986, abandoned, which is a continuation of Ser. No. 628,128, Jul. 9, 1984, abandoned, which is a continuation of Ser. No. 439,527, Nov. 4, 1982, abandoned, which is a continuation of Ser. No. 251,685, Apr. 6, 1981, abandoned.

[51] Int. Cl.$^4$ .................. A01N 25/00; A01N 37/52; A01N 43/54; A01N 43/62
[52] U.S. Cl. ..................... 514/275; 424/84; 514/218; 514/632
[58] Field of Search ............... 514/218, 275, 632; 424/84

[56] References Cited

U.S. PATENT DOCUMENTS

| | | | |
|---|---|---|---|
| 3,878,201 | 4/1975 | Tomcufcik | 540/553 |
| 4,087,525 | 5/1978 | Lovell | 514/219 |
| 4,163,102 | 7/1979 | Lovell | 544/330 |
| 4,353,907 | 10/1982 | Lovell | 514/275 |

FOREIGN PATENT DOCUMENTS

| | | |
|---|---|---|
| 755598 | 2/1971 | Belgium . |
| 2408001 | 8/1975 | Fed. Rep. of Germany . |
| 39-4500 | 4/1964 | Japan . |
| 53-118524 | 10/1978 | Japan . |

OTHER PUBLICATIONS

The Merck Index 9th Ed. (1976), pp. 268+269.

*Primary Examiner*—Allen J. Robinson
*Attorney, Agent, or Firm*—C. J. Fickey

[57] ABSTRACT

A solid, non-particulate, non-flowable, non-repellant insecticide bait composition for consumer household control of cockroaches, comprises a pentadienone hydrazone insecticide compound, a food attractant system, and a binder.

4 Claims, No Drawings

NON-PARTICULATE, NON-FLOWABLE, NON-REPELLANT INSECTICIDE-BAIT COMPOSITION FOR THE CONTROL OF COCKROACHES

This application is a continuation of application Ser. No. 933,331, filed Nov. 19, 1986, now abandoned; which was a continuation of application Ser. No. 628,128, filed July 9, 1984, now abandoned; which was a continuation of application Ser. No. 439,527 filed Nov. 4, 1982, now abandoned; which was a continuation of application Ser. No. 251,685, filed Apr. 6, 1981 now abandoned.

The present invention relates to solid, non-particulate, non-flowable, non-repellant, fully edible insecticide-bait compositions for the consumer control of cockroaches. More particularly, it relates to insecticide-bait compositions comprising a pentadienone hydrazone insecticide compound, a specific food attractant system, and a binder. A preservative is optionally added to the composition.

Pentadiene-3-one substituted amidinohydrazones are described by Tomcufcik, U.S. Pat. No. 3,878,201, as anti-malarial and anti-tubercular agents. Lovell, U.S. Pat. Nos. 4,087,525 and 4,163,102—the disclosures of which are incorporated hereby by reference thereto, describes the use of these compounds as insecticides. The insecticide compounds of the Lovell patents are generally represented by the formula:

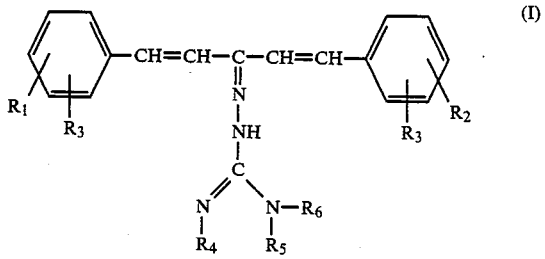

wherein $R_1$ and $R_2$ each represent hydrogen, halogen, the group $-CF_3$, $C_1-C_4$ alkyl, $C_1-C_4$ alkoxy, or $C_1-C_4$ alkylthio; $R_3$ is hydrogen or methyl, provided that when $R_3$ is methyl both $R_1$ and $R_2$ are also methyl; $R_4$ and $R_5$ represent hydrogen, $C_1-C_4$ alkyl or, when taken together, an alkylene group of 2 to 6 carbon atoms, methyl or phenyl alkylene group of 2 to 4 carbon atoms or 1,2-cyclohexylene; $R_6$ is hydrogen or $C_1-C_4$ alkyl; and salts thereof.

Particularly useful compounds are those represented by the formula:

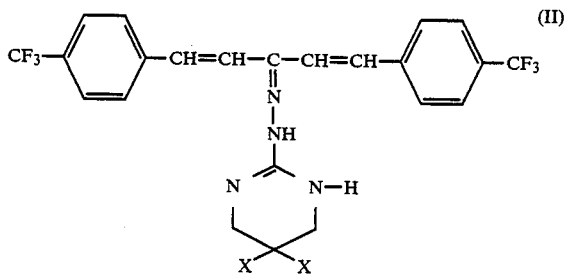

wherein X is hydrogen or methyl. The efficacy of the compounds represented by formulas (I) and (II) against a variety of Lepidopterous, Orthopterous, Dipterous and Hymenopterous insects is also described by Lovell.

However, the form and method for use described in these patents is generally related to agricultural applications where particulate baits are used and distributed over wide, open areas, and the types of bait systems suggested therein are clearly not suitable for general household consumer use, where an insecticide or insecticide-impregnated material may come into contact with and/or be ingested by children or domestic pets. Further, the types of food materials suggested by these patents have been found by Applicants to be unacceptable in a consumer product formulation in that the product is deficient in one or both of the following characteristics necessary for an acceptable consumer product: non-flowability over the range of temperatures typically encountered during shipping and storage conditions ("non-flowable", as used in the instant specifications and claims, being defined as non-flowable over the range of temperatures typically encountered during shipment and storage conditions) and total edibility by the cockroaches so that uneaten, insecticide-impregnated material will not pose a hazard to children or domestic animals. There is a need, therefore, for a form for delivery of these insecticides suitable for use by the ordinary householder for the control of cockroaches, and a formulation which both possesses the foregoing characteristics and is efficacious in killing cockroaches.

The present invention provides solid, non-particulate, non-flowable, non-repellant, fully edible insecticide-bait compositions comprising from about 0.25% to about 5% by weight of a pentadienone substituted amidinohydrazone compound (I), in combination with a food attractant system, and a non-repellant water-soluble binder. The insecticide-bait composition may further comprise a water-soluble preservative in order to, inter alia, enhance the shelf life of the composition.

Preferably, the invention provides such an insecticide-bait composition comprising an insecticide compound represented by formula (II), and particularly the compound 1,5-bis(α,α,α-trifluoro-p-tolyl)-1,4-pentadien-3-one(1,4,5,6-tetrahydro-5,5-dimethyl-2-pyrimidinyl)hydrazone (III), wherein the groups X in formula (II) are each methyl. The insecticide-bait compositions of the invention, which are cohesive solids at room temperature, may take any convenient form, such as wafers, pellets, molded caps, and the like.

The food attractant system used in the composition of the present invention comprises a mixture of a liquid food selected from the group consisting of molasses, corn syrup, maple syrup, honey, and mixtures of two or more of these foods, and a solid food-oatmeal. The amount of food attractant system and binder material used in the insecticide-bait compositions, and the ratio of one to the other, is not critical provided they form a cohesive solid at room temperature. Generally, the liquid food comprises about 20 to 50%, preferably 35 to 45%, by weight of the composition, and the oatmeal comprises about 25 to 75%, preferably 30 to 45%, by weight, of the composition.

The non-repellent binder material used in the composition of the present invention is a solid or liquid, hydrophilic or lipophilic, water-soluble material which is fully edible by the cockroaches. Such substances include, for example, polyethylene glycols of the type available from Union Carbide Corp. under the Carbowax ™ name. Carbowax ™ 8000 is the preferred binder material. The binder material generally comprises about 10 to 55%, preferably 12 to 20%, by weight, of the composition.

The insecticide compound is, in general, not sufficiently soluble in the binder material. Although the solid insecticide compound may be incorporated into the binder in the form of discrete solid particles, it is preferable to convert the compound to a more readily dispersible form. It has been found that $C_8$–$C_{18}$ organic fatty acids are particularly useful in converting the insecticide into a form dispersible in the binder material. The fatty acid salt of the insecticide forms a dispersed internal phase in the continuous binder phase. Other acid salts, such as those obtained by reacting the insecticide with surfactants containing fatty acid groups, certain water-soluble acid salts such as acetates, lactates, propionates, sulfates, sulfonates, and the like, may also be useful in the dispersion of the insecticide in the binder. Generally the insecticide compound is dispersed by reaction with at least an equimolar amount of acid. Preferably, a molar excess of the acid is used. Preferred insecticide-bait compositions are obtained containing from about 1% to 3%, by weight, of the insecticide compound and 1% to 3%, by weight, of the fatty acid. Oleic acid is a preferred fatty acid.

The preferred compositions may be readily prepared by a hot melt technique, whereby a dispersion of the acid salt of the insecticide compound in a suitable organic solvent, preferably isopropanol, is added to a fluid heated mixture of food attractant and binder and then poured or cast into a suitable mold or cap, and cooled to room temperature.

As aforesaid, a suitable non-repellant preservative may also be incorporated into the composition to prevent spoilage thereof. When used, the preservative should be palatable to the cockroaches (dihydroacetic acid, for example, does not satisfy this requirement). A preferred preservative is the cis isomer of 1-(3-chloroallyl)3,5,7-triaza-1-azonia-adamantane chloride, commercially available from Dow Chemical Company as Dowicil ™ 200, and when used, it will generally comprise at least about 0.2%, preferably about 0.2 to 0.5%, by weight of the composition.

The preferred compositions of the invention are advantageously used in a child and pet-resistance device, which is, however, open and attractive to the insects. Such a device is described, for example, in commonly assigned, copending application, Ser. No. 406,671, filed Aug. 12, 1982.

The invention is more completely described and illustrated by the following non-limiting examples:

EXAMPLE 1

Corn Syrup (400 grams), oatmeal (380 grams) and Carbowax ™ 8000 (118 grams; polyethylene glycol obtained from Union Carbide Corp.) were mixed and heated to about 70° C. A dispersion of insecticide compound (III), 20 grams, was prepared in 20 grams of oleic acid and 60 grams of isopropanol; 2 grams of Dowicil ™ 200 was added. The insecticide solution was poured into the heated food-binder mixture, mixed thoroughly and then cast into small caps and cooled to room temperature.

EXAMPLE 2

In order to test the efficacy of the insecticide-bait composition of Example 1, the bait was placed in a device of the type described in the aforementioned U.S. application Ser. No. 406,671, now abandoned, and compared to BOLT ® bait currently marketed by S. C. Johnson & Son, Inc. It is believed that the BOLT ® bait is described in U.S. Pat. No. 4,049,460 wherein the insecticide is a phosphorothioate compound and its percent concentration is 0.5%, by weight. The BOLT ® bait contains dog food (which is not fully edible by the cockroaches) and possibly maltose and/or brown sugar as the food attractant(s). The device in which the BOLT ® bait is placed does, if anything, alloww easier access to the bait therein by cockroaches than does the device into which Applicants' bait was placed.

In Long Island, N.Y., each of the baits of Example 1 and BOLT ®, in their respective devices, wee placed in eighteen (18) apartments, for which the average precount of the number of cockroaches in each apartment was greater than 1000, at the rate of twelve (12) per 100 square feet.

Table I shows the average percent reduction in cockroach population (determined by the formula:

$$\frac{\text{Sum of Precounts} - \text{Sum of Post-counts}}{\text{Sum of Precounts}} \times 100)$$

at the treatment time shown:

TABLE I

| Insecticide-Bait | Average Percent Reduction In Cockroach Population | | |
|---|---|---|---|
| | 2 Weeks | 1 Month | 2 Months |
| Example 1 | 72 | 85 | 93 |
| BOLT ® | 34 | 22 | 62 |

The data clearly shows that the insecticide-bait composition of Example 1 is superior to the BOLT ® product.

EXAMPLE 3

The test of Example 2 was repeated in Los Angeles, Calif., except that the insecticide baits were distributed in fifty-six (56) apartments each, at the rate of 4 to 6 per 100 square feet, and the average precount of cockroaches in the apartments in which the insecticide-bait of Example 1 was placed was 116 whereas the average precount of cockroaches in which the BOLT ® bait product was placed was 27.

Table II shows the average percent reduction in roach population (determined as in Example 2) at the treatment time shown:

TABLE II

| Insecticide-Bait | Average Percent Reduction In Cockroach Population | | |
|---|---|---|---|
| | 1 month | 2 months | 3 months |
| Example 1 | 80.5 | 86.3 | 90.3 |
| BOLT ® | 0 | 0 | 0 |

As can be seen, the BOLT ® bait product showed no reduction in the roach population, whereas the insecticide-bait composition of Example 1 showed very significant population reduction in the apartments treated.

EXAMPLE 4

The insecticide bait composition of Example 1 was tested for efficacy against German and American cockroaches according to the following procedure:

Ten (10) German cockroaches were placed in each of three (3) 16 oz. wide mouth jars with a food source (dog food), water and harborage and were permitted to acclimate to this environment for two (2) days before insecticide-bait placement. The insecticide-bait was contained in a bottle cap to minimize experimental variations. The same procedure was followed with ten (10) American cockroaches. Mortality counts were taken, and the average results are shown in Table III.

TABLE III

| Day | Average Mortality Rate | |
|---|---|---|
| | German Cockroaches | American Cockroaches |
| 3 | 83.3 | 10 |
| 4 | 90.0 | 36.7 |
| 5 | 93.3 | 80 |
| 6 | 93.3 | 90 |
| 7 | 96.7 | 100 |
| 10 | 100 | |

EXAMPLE 5

The procedure of Example 4 was repeated, except that peanut butter containing 2%, by weight, of the compound III was substituted for the insecticide-bait composition of Example 1. Mortality counts were taken, and the average results are shown in Table IV.

TABLE IV

| Day | Average Mortality Rate | |
|---|---|---|
| | German Cockroaches | American Cockroaches |
| 3 | 70 | 5 |
| 4 | 90 | 5 |
| 5 | 95 | 10 |
| 6 | 95 | 10 |
| 7 | 95 | 15 |
| 10 | 100 | 70 |
| 11 | | 75 |
| 12 | | 85 |
| 13 | | 85 |
| 14 | | 90 |
| 17 | | 100 |

As can be seen from a comparison of the data in Tables III and IV, the average mortality rate of German cockroaches was roughly equivalent, but it required 15 days (17 days less the 2 day acclimation period) to achieve 100 percent mortality of American cockroaches with the peanut butter-insecticide composition whereas the insecticide-bait composition of Example 1 achieved 100% mortality in only 5 days. And, an additional disadvantage of the peanut butter bait is that peanut butter will flow at a relatively low temperature making it unacceptable for use in a consumer product which may be subjected to elevated temperatures during shipping and/or storage.

EXAMPLE 6

The procedure of Example 4 was again repeated, except that corn cob grits containing 30%, by weight, soybean oil and 0.88%, by weight, of the compound III was substituted for the insecticide-bait composition of Example 1. Mortality counts were taken, and the average results are shown in Table V.

TABLE V

| Day | Average Mortality Rate | |
|---|---|---|
| | German Cockroaches | American Cockroaches |
| 3 | 3.3 | 0 |
| 4 | 3.3 | 0 |
| 5 | 3.3 | 0 |
| 6 | 3.3 | 0 |
| 7 | 3.3 | 0 |
| 10 | 3.3 | 0 |
| 11 | 3.3 | 0 |
| 12 | 3.3 | 0 |
| 13 | 3.3 | 0 |
| 14 | 3.3 | 0 |
| 17 | 3.3 | 0 |
| 18 | 3.3 | 3.3 |
| 19 | 3.3 | 3.3 |
| 20 | 3.3 | 3.3 |
| 21 | 3.3 | 3.3 |

Comparison of the data in Table V with that of Table III clearly indicates that superiority of the insecticide-bait composition of the present invention. Additionally, the corn cob grits are not fully edible by the cockroaches, thereby creating a problem of residual insecticide-containing material being present in a household, possibly coming into contact with or being ingested by children or domestic pets. Further, the soybean oil poses rancidity problems which makes its incorporation into a consumer product undesirable.

What is claimed is:

1. A solid, non-particulate, non-repellant, non-flowable, fully edible insecticidal bait composition consisting essentially of about 0.25 to 5%, by weight, of an insecticide compound which is a salt of 1,5-bis($\alpha,\alpha,\alpha$-trifluoro-p-tolyl)-1,4pentadiene-3-one(1,4,5,6-tetrahydro-5,5-dimethyl-2-pyrimidinyl)-hydrazone and a $C_8$ to $C_{18}$ fatty acid, a food attractant system consisting essentially of oatmeal, and a liquid food of the group corn syrup, molasses, maple syrup or honey, said liquid food being about 20 to 50%, by weight, of the composition and said oatmeal being about 25 to 75%, by weight, of the composition, about 10 to 55%, by weight, of the composition, of a water-soluble polyethylene glycol binder material, and at least about 0.2%, by weight, of the cis isomer of 1-(3-chloroallyl)-3,5,7-triaza-1-azonia-adamantane chloride as a preservative.

2. The composition of claim 1 wherein the 1,5-bis-($\alpha,\alpha,\alpha$-trifluoro-5,5-dimethyl-2-pyrimidinyl)hydrazone and $C_8$ to $C_{18}$ fatty acid salt is about 1 to 3%, by weight, of the composition, the liquid food is about 35 to 45%, by weight, of the composition, the oatmeal is about 30 to 45%, by weight, of the composition, the binder is about 12 to 20%, by weight, of the composition, and the preservative is about 0.2 to 0.5%, by weight, of the composition.

3. The composition of claim 1 wherein the fatty acid is oleic acid.

4. The composition of claim 1 wherein the salt is dispersed in isopropanol in a ratio of about 1:3.

* * * * *